(12) United States Patent
Jin et al.

(10) Patent No.: US 12,702,386 B2
(45) Date of Patent: Aug. 11, 2026

(54) ULTRASONIC IMAGING APPARATUS AND CONTROL METHOD THEREOF

(71) Applicant: Samsung Medison Co., Ltd., Gangwon-do (KR)

(72) Inventors: Gilju Jin, Seoul (KR); Mijeoung Ahn, Seoul (KR); Seungju Lee, Seoul (KR)

(73) Assignee: SAMSUNG MEDISON CO., LTD., Gangwon-Do (KR)

(*) Notice: Subject to any disclaimer, the term of this patent is extended or adjusted under 35 U.S.C. 154(b) by 36 days.

(21) Appl. No.: 18/592,282

(22) Filed: Feb. 29, 2024

(65) Prior Publication Data

US 2024/0225612 A1 Jul. 11, 2024

Related U.S. Application Data

(63) Continuation-in-part of application No. 17/164,044, filed on Feb. 1, 2021, now Pat. No. 12,508,002, which (Continued)

(30) Foreign Application Priority Data

Jun. 15, 2015 (KR) ........................ 10-2015-0084057

(51) Int. Cl.
*A61B 8/00* (2006.01)
*A61B 8/08* (2006.01)
(Continued)

(52) U.S. Cl.
CPC ............ *A61B 8/523* (2013.01); *A61B 8/0816* (2013.01); *A61B 8/0866* (2013.01); *A61B 8/14* (2013.01);
(Continued)

(58) Field of Classification Search
None
See application file for complete search history.

(56) References Cited

U.S. PATENT DOCUMENTS 8,083,678 B2 12/2011 Abuhamad
8,262,572 B2 9/2012 Chono
(Continued)

FOREIGN PATENT DOCUMENTS

EP 2296011 A2 3/2011
EP 2679158 A1 1/2014
(Continued)

OTHER PUBLICATIONS

Korean Notice of Allowance dated Jun. 18, 2022 issued in Korean Patent Application No. 10-2015-0084057.
(Continued)

*Primary Examiner* — Yi-Shan Yang
(74) *Attorney, Agent, or Firm* — Morgan Lewis & Bockius LLP

(57) ABSTRACT

Disclosed herein is an ultrasonic imaging apparatus and a control method thereof. The ultrasonic imaging apparatus includes a display, and at least one processor. The at least one processor obtains ultrasound image data acquired by an ultrasonic probe, recognizes at least one anatomical feature from the obtained ultrasound image data, automatically acquires at least one reference plane image based on the recognized at least one anatomical feature, and displays the acquired at least one reference plane image on the display.

20 Claims, 21 Drawing Sheets

Related U.S. Application Data is a continuation of application No. 15/166,071, filed on May 26, 2016, now Pat. No. 10,932,756.

(51) Int. Cl.
*A61B 8/14* (2006.01)
*G06T 7/73* (2017.01)

(52) U.S. Cl.
CPC .............. *A61B 8/4245* (2013.01); *A61B 8/46* (2013.01); *A61B 8/483* (2013.01); *G06T 7/73* (2017.01); *A61B 8/461* (2013.01); *G06T 2207/10132* (2013.01); *G06T 2207/30016* (2013.01); *G06T 2207/30244* (2013.01)

(56) References Cited

U.S. PATENT DOCUMENTS

| | | | | |
|---|---|---|---|---|
| 8,915,855 | B2 | 12/2014 | Lee | |
| 9,332,965 | B2 | 5/2016 | Lee et al. | |
| 10,433,819 | B2 | 10/2019 | Lee et al. | |
| 10,932,753 | B2 | 3/2021 | Tanaka et al. | |
| 11,881,309 | B2 | 1/2024 | Allassonniere et al. | |
| 2004/0097806 | A1 | 5/2004 | Hunter | |
| 2004/0122310 | A1* | 6/2004 | Lim | A61B 8/0816 600/443 |
| 2005/0004465 | A1 | 1/2005 | Abuhamad | |
| 2009/0093717 | A1 | 4/2009 | Carneiro et al. | |
| 2010/0307516 | A1 | 12/2010 | Neubauer | |
| 2011/0054324 | A1 | 3/2011 | Lee | |
| 2013/0057547 | A1 | 3/2013 | Hwang et al. | |
| 2013/0072797 | A1 | 3/2013 | Lee | |
| 2013/0324849 | A1 | 12/2013 | Park | |
| 2014/0100440 | A1 | 4/2014 | Cheline et al. | |
| 2014/0153358 | A1 | 6/2014 | Balakrishnan | |
| 2014/0253358 | A1 | 9/2014 | Lorenz | |
| 2015/0190653 | A1 | 7/2015 | Bharat | |
| 2015/0302638 | A1 | 10/2015 | Jago | |
| 2016/0018520 | A1* | 1/2016 | Hirai | G01S 15/8977 367/11 |
| 2017/0367685 | A1* | 12/2017 | Zou | G06F 18/22 |
| 2021/0153847 | A1 | 5/2021 | Yoo et al. | |
| 2022/0071595 | A1 | 3/2022 | Mienkina et al. | |
| 2022/0087644 | A1* | 3/2022 | Patil | G16H 40/63 |
| 2025/0148669 | A1* | 5/2025 | Dickie | G06T 7/12 |

FOREIGN PATENT DOCUMENTS

| | | | |
|---|---|---|---|
| EP | 3964136 | A1 | 3/2022 |
| JP | 2008-259764 | A | 10/2008 |
| JP | 2013-123582 | A | 6/2013 |
| JP | 2014-28132 | A | 2/2014 |
| JP | 5491405 | B2 | 5/2014 |
| KR | 10-1121379 | B1 | 3/2012 |
| KR | 10-2014-0024190 | A | 2/2014 |
| KR | 10-2016-0016467 | A | 2/2016 |
| KR | 10-2016-0147386 | A | 12/2016 |
| WO | 2004/093687 | A1 | 11/2004 |
| WO | 2014/080319 | A1 | 5/2014 |

OTHER PUBLICATIONS

Korean Office Action dated Nov. 14, 2022 issued in Korean Patent Application No. 10-2022-0117892 (with English translation).
European Notice of Allowance dated Jan. 11, 2021 issued in European Patent Application No. 15178609.2.
European Office Action dated Jan. 2, 2020 issued in European Patent Application No. 15178609.2.
Sonio Diagnostics—Caso clinico | Sindrome de Charge, https://youtu.be/laYLsi_-nac?si=P9EBmtHqorrbwE_g.
Extended European Search Report dated Oct. 21, 2016 issued in European Patent Application No. 15178609.2.
U.S. Notice of Allowance dated Oct. 28, 2020 issued in U.S. Appl. No. 15/166,071.
U.S. Non-Final Office Action dated Apr. 29, 2020 issued in U.S. Appl. No. 15/166,071.
U.S. Final Office Action dated Sep. 3, 2019 issued in U.S. Appl. No. 15/166,071.
U.S. Non-Final Office Action dated Feb. 19, 2019 issued in U.S. Appl. No. 15/166,071.
U.S. Final Office Action dated Oct. 2, 2023 issued in U.S. Appl. No. 17/164,044.
U.S. Non-Final Office Action dated Apr. 20, 2023 issued in U.S. Appl. No. 17/164,044.
U.S. Non-Final Office Action dated Dec. 9, 2022 issued in U.S. Appl. No. 17/164,044.
Korean Office Action dated Jan. 10, 2022 issued in Korean Patent Application No. 10-2015-0084057 (with English translation).
Office Action dated Oct. 11, 2024, issued in corresponding Korean Patent Application No. 10-2024-0110763 with an English translation.

* cited by examiner

Figure 2:
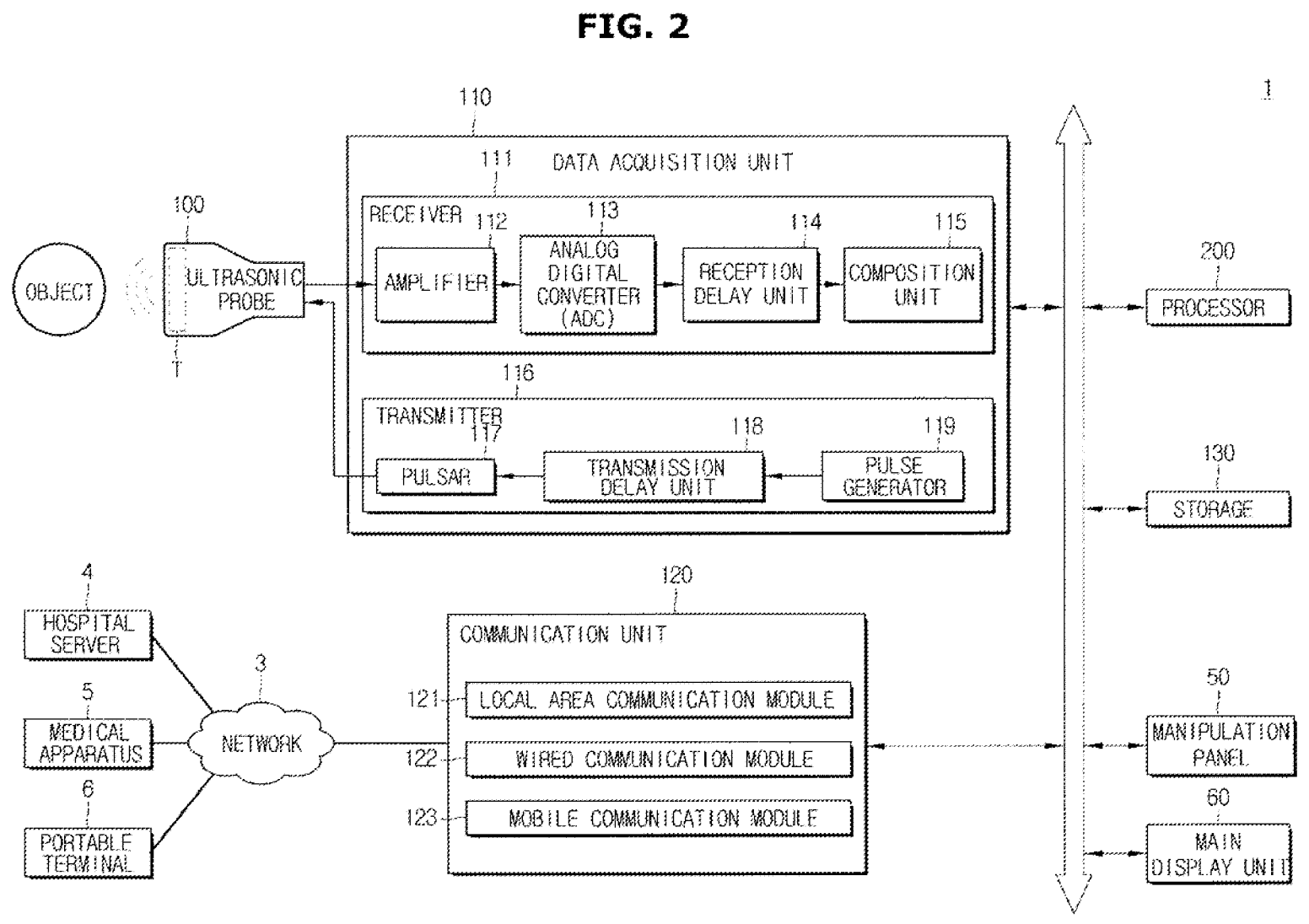

OBJECT

100 ULTRASONIC PROBE

110 DATA ACQUISITION UNIT

111 RECEIVER

112 AMPLIFIER

113 ANALOG DIGITAL CONVERTER (ADC)

114 RECEPTION DELAY UNIT

115 COMPOSITION UNIT

116 TRANSMITTER

117 PULSAR

118 TRANSMISSION DELAY UNIT

119 PULSE GENERATOR

200 PROCESSOR

130 STORAGE

50 MANIPULATION PANEL

60 MAIN DISPLAY UNIT

120 COMMUNICATION UNIT

121 LOCAL AREA COMMUNICATION MODULE

122 WIRED COMMUNICATION MODULE

123 MOBILE COMMUNICATION MODULE

3 NETWORK

4 HOSPITAL SERVER

5 MEDICAL APPARATUS

6 PORTABLE TERMINAL

FIG.3
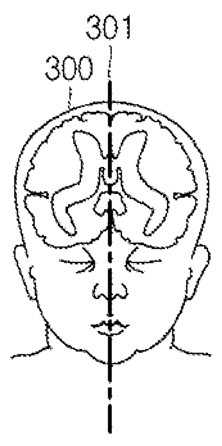
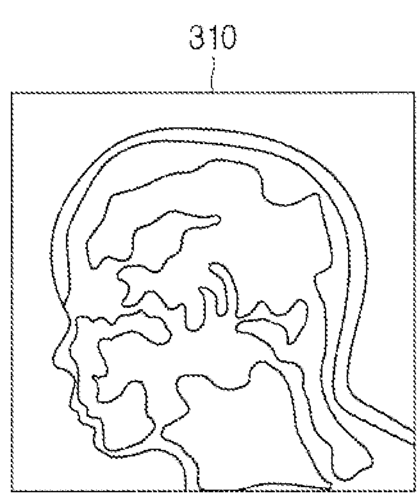

ULTRASONIC IMAGING APPARATUS AND CONTROL METHOD THEREOF

CROSS-REFERENCE TO RELATED APPLICATION

This application is a continuation-in-part of U.S. patent application Ser. No. 17/164,044, filed on Feb. 1, 2021, which is a continuation of U.S. patent application Ser. No. 15/166,071, filed on May 26, 2016, which claims the benefit of Korean Patent Application No. 10-2015-0084057, filed on Jun. 15, 2015 in the Korean Intellectual Property Office, the disclosures of which are incorporated herein by reference.

BACKGROUND

1. Field

Embodiments of the present disclosure relate to an ultrasonic imaging apparatus configured to be used easily, and a control method of the same.

2. Description of the Related Art

An ultrasonic imaging apparatus irradiates ultrasound signals to a target part inside an object from the surface of an object, and noninvasively acquires section images about soft tissue of the object or images about blood vessels of the object by using echo ultrasound signals reflected from the object.

An ultrasonic imaging apparatus is compact, inexpensive, and displaying a diagnostic imaging immediately as compared with another type of diagnostic imaging apparatus, e.g., X-ray device, Magnetic Resonance Image (MRI), diagnostic nuclear medical apparatus. In addition, the ultrasonic imaging apparatus is safe because there is no risk of radiation exposure. Therefore, the ultrasonic imaging apparatus is widely used in medical examination at cardiology, abdomen, urology, and maternity clinics.

An ultrasonic imaging apparatus is widely used to diagnose the condition of fetus, but there are difficulties in acquiring an appropriate ultrasound image to diagnosis the condition of fetus.

SUMMARY

Therefore, it is an aspect of the present disclosure to provide an ultrasonic imaging apparatus capable of easily extracting a reference plane and a control method of the ultrasonic imaging apparatus.

Additional aspects of the disclosure will be set forth in part in the description which follows and, in part, will be obvious from the description, or may be learned by practice of the disclosure.

In accordance with one aspect of the present disclosure, an ultrasonic imaging apparatus includes an acquisition unit configured to acquire a volume data of an object and a processor configured to determine whether an acquisition position of the volume data is within an allowable range by using pre-stored landmark information and configured to acquire a plurality of reference planes from the volume data when the acquisition position of the volume data is within the allowable range.

The pre-stored landmark information may include a landmark about at least one of reference plane among the plurality of reference planes.

The pre-stored landmark information may include a landmark commonly existed in the plurality of reference planes and a landmark distinctively existed in each reference plane of the plurality of the reference planes. For example, the pre-stored landmark information may include at least one of Cavum septum pellucidum (CSP), Cerebellum, Choroid plexus, Lateral ventricle, Cisterna magna, and Thalami. The processor may determine whether the acquisition position of the volume data is within the allowable range by comparing a similarity between at least one plane extracted from the volume data and the landmark about the reference plane.

The processor may provide a first feedback to a user when the acquisition position of the volume data is determined to be within the allowable range. At this time, the first feedback may include at least one of a tactile feedback, a visual feedback and an auditory feedback.

The processor may provide a second feedback to a user when the acquisition position of the volume data is determined to be out of the allowable range. At this time, the processor may estimate a relative position of the volume data with respect to the allowable range, and may generate the second feedback based on the relative position. In addition, the second feedback may be differently generated according to the relative position of the volume data with respect to the allowable range.

The processor may provide a third feedback when the volume data is acquired by scanning an object asymmetrically.

The allowable range may include at least two planes among the plurality of reference planes.

In accordance with another aspect of the present disclosure, a control method of an ultrasonic imaging apparatus includes acquiring a volume data of an object, determining whether an acquisition position of the volume data is within an allowable range by using pre-stored landmark information, and extracting a plurality of reference planes from the volume data when the acquisition position of the volume data is within the allowable range.

The determining of acquisition position may include comparing a similarity between at least one plane extracted from the volume data and landmark information of the reference plane, and determining that the position of the volume data is within the allowable range when the similarity is larger than a threshold.

The control method may further include providing a first feedback to a user when the acquisition position of the volume data is within the allowable range.

The control method may further include estimating a relative position of the volume data with respect to the allowable range when the acquisition position of the volume data is determined to be out of the allowable range, and generating and providing a second feedback based on the relative position.

The control method may further include extracting a plane from the volume data, determining of symmetry of the extracted plane, and providing a third feedback when the extracted plane is asymmetrical.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 2 is a control block diagram illustrating an ultrasonic imaging apparatus according to an embodiment of the present disclosure;

FIGS. 3 and 4 are views schematically illustrating an image of a reference plane of fetus;

DETAILED DESCRIPTION

Hereinafter 'ultrasound image' may represent an image of an object acquired by using ultrasonic waves, and 'an object' may represent a human, an animal or a part of a human or animal. The ultrasound image may include a three dimensional (3D) volume image as well as a two dimensional (2D) cross sectional image.

An object may include liver, heart, uterus, brain, breasts, or blood vessel, and hereinafter for the convenience of description, the object is limited to fetus inside a mother.

In addition, hereinafter a user may be a medical professional, e.g., a doctor, a nurse, a medical technologist or a medical imaging professional, and a technician capable of serving medical apparatuses may become the user, but is not limited thereto.

Figure 1:
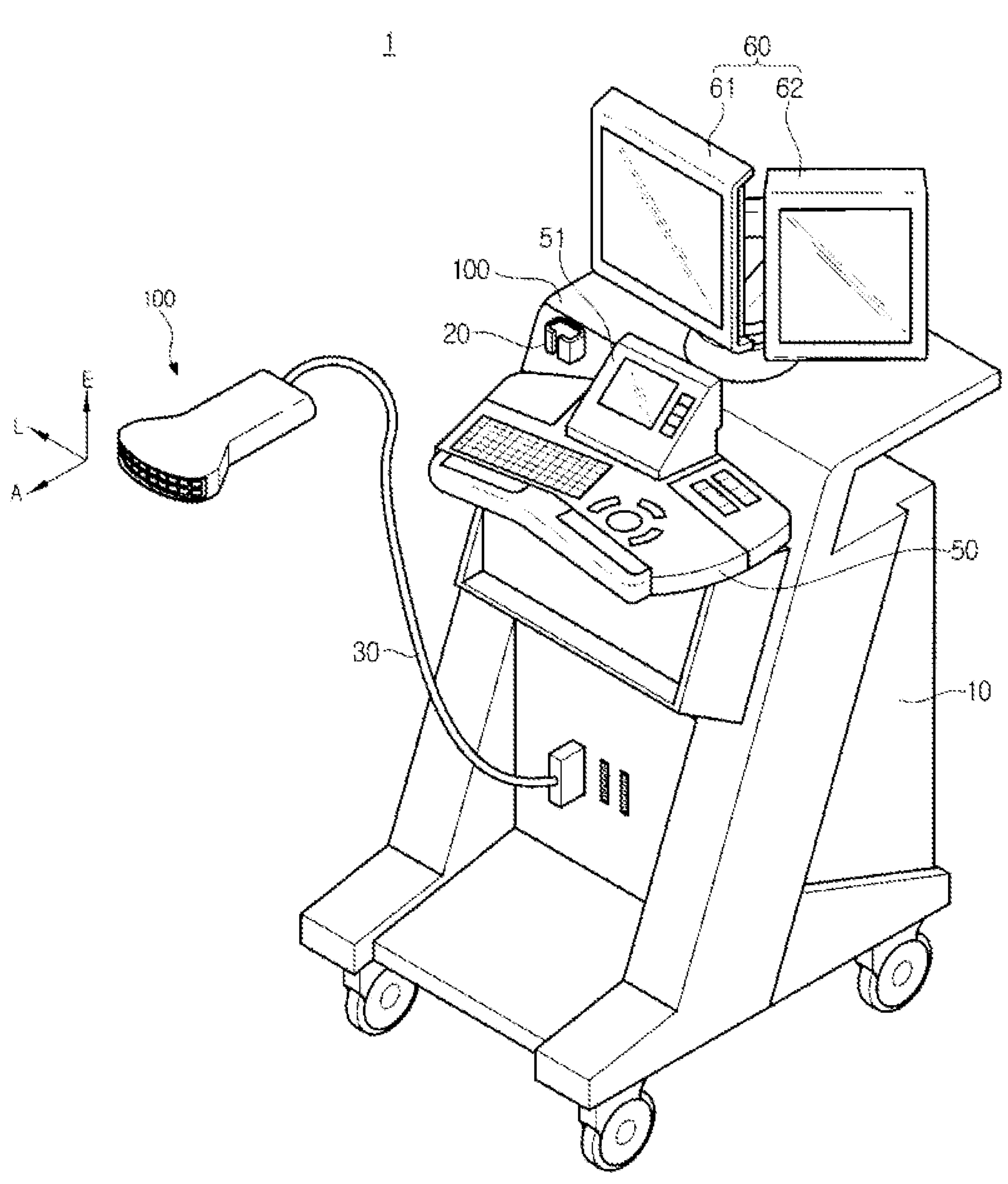
FIG. 1 is a perspective view illustrating an exterior of an ultrasonic imaging apparatus according to an embodiment of the present disclosure.

FIG. 1 is a perspective view illustrating an exterior of an ultrasonic imaging apparatus according to an embodiment of the present disclosure and FIG. 2 is a control block diagram illustrating an ultrasonic imaging apparatus according to an embodiment of the present disclosure.

Referring to FIGS. 1 and 2, an ultrasonic imaging apparatus 1 may include a body 10, an ultrasonic probe 100, a manipulation panel 50, and a display unit 60.

The ultrasonic probe 100 may be a part configured to scan an object ob by making contact with a surface of the ob, and may transmit ultrasonic signal to the object ob according to a driving signal or may receive an echo signal reflected from the object ob.

A direction, which is scanned by the ultrasonic probe 100, may be defined as an axis direction A, a lateral direction L, and an elevation direction E. The direction A may represent a direction in which ultrasonic waves are irradiated, the direction L may represent a direction in which transducers T form a row, and the direction E may represent a direction perpendicular to the direction A and the direction L.

The ultrasonic probe 100 may include a plurality of transducers T. The transducer T may convert an ultrasound signal into an electrical signal or vice versa.

Each transducer T may be implemented by a magnetostrictive ultrasonic transducer using the magnetostrictive effect of a magnetic material, a piezoelectric ultrasonic transducer using the piezoelectric effect of a piezoelectric material, piezoelectric micromachined ultrasonic transducer (pMUT) or a capacitive micromachined ultrasonic transducer (hereinafter referring to cMUT) that transmits and receives ultrasonic waves using vibration of several hundreds or thousands of micromachined thin films.

The transducers T may be arranged in an array. For example, the transducers T may be arranged in a linear array, in a convex array, in a phased array, or in a sector array. In addition, the transducers T may be arranged in a multiple dimensional array, e.g., M*N array.

When the transducers T are arranged in one dimension, the ultrasonic probe 100 may acquire an ultrasonic signal of a space of an object by swing the array of the transducers T in the direction E, and when the transducers T are arranged in multiple dimensional array, the ultrasonic probe 100 may acquire an ultrasonic signal of a space of an object by a single transmission of ultrasonic waves.

The ultrasonic probe 100 may be connected to the body 10 of the ultrasonic imaging apparatus 1 via a cable 30 to receive various signals, which are needed for control of the ultrasonic probe 100, from the body 10. In addition, the ultrasonic probe 100 may transmit an analog signal or a digital signal corresponding to an echo signal received by the ultrasonic probe 100, to the body 10.

A data acquisition unit 110 may form an ultrasonic signal transmitted from the ultrasonic probe 100 or may composite an echo signal outputted from the ultrasonic probe 100. As mentioned above, an echo signal which is composited in the data acquisition unit 110 may be referred to as ultrasound data, and an ultrasound data about a 3D volume may be referred to as a volume data. When the generated ultrasound data corresponds to a cross-section of the object, a volume data may be configured with a plurality of ultrasound data of different cross sections.

The data acquisition unit 110 may include a receiver 111 and a transmitter 116. The transmitter 116 may supply a driving signal to the ultrasonic probe 100, and may include a pulse generator 119, a transmission delay unit 118, and a pulsar 117.

The pulse generator 119 may generate a pulse to form transmission ultrasonic waves according to a certain Pulse Repetition Frequency (PRF), and the transmission delay unit 118 may apply a delay time to a pulse to determine transmission directionality. Each pulse in which a delay time is applied may correspond to each transducer T included in the ultrasonic probe 100. The pulsar 117 may apply a driving signal or a driving pulse, which is a timing corresponding to each pulse in which a delay time is applied.

The receiver 111 may generate ultrasound data by processing an echo signal received from the ultrasonic probe 100, and may include an amplifier 112, an Analog Digital converter (ADC) 113, a reception delay unit 114, and a composition unit 115. The amplifier 112 may amplify an echo signal inputted through a channel, and the ADC 113 may perform analog-digital conversion on an amplified echo signal. The reception delay unit 114 may apply a delay time to an echo signal, which is converted into a digital, to determine reception directionality, and the composition unit 115 may generate ultrasound data by compositing an echo signal, which is processed by the reception delay unit 114.

Meanwhile, the receiver 111 may not include the amplifier 112 according to the type of the implementation of the receiver 111. That is, when the sensibility of the ultrasonic probe 100 is improved or when the number of processing bits of the ADC 113 is improved, the amplifier 112 may be omitted.

Meanwhile, FIG. 1 illustrates a case in which the ultrasonic probe 100 and the data acquisition unit 110 are separately provided, but the ultrasonic probe 100 and the data acquisition unit 110 may be integrally provided.

The manipulation panel 50 may receive an input of a control command related to operations of the ultrasonic imaging apparatus 1. The user may input a diagnosis start command, a command for selecting an area to be diagnosed, a command for selecting a diagnosis type, and a command for selecting a display mode of an image to be output, through the manipulation panel 50. The display mode may include an Amplitude mode (A mode), a Brightness mode (B mode), a Doppler mode (D mode), an Elastography mode (E mode), and a Motion mode (M mode).

The manipulation panel 50 may receive an input of a command of generating a 3D volume image, and a command of extracting a reference plane. In addition, the user may input direction and location information which are needed to extract a reference plane by using the manipulation panel 50.

In addition, the manipulation panel 50 may be implemented by button input devices, e.g., push button, membrane button, and touch input device, e.g., touch pad, but is not limited thereto. For example, the manipulation panel 50 may be implemented by an input device, e.g., a joystick, a track ball, a knob, and a dial.

The manipulation panel 50 may further include a sub display unit 51. The sub display unit 51 may be provided on one side of the manipulation panel 50 to display information related to a manipulation of the ultrasonic imaging apparatus 1.

For example, the sub display unit 51 may display menus and guidance needed for setting the ultrasonic imaging apparatus 1 and may display current setting of the ultrasonic imaging apparatus 1.

The sub display unit 51 may be implemented by a Liquid Crystal Display (LCD), a Light Emitting Diodes (LED), an Organic Light Emitting Diodes (OLED) or a touch panel. When the sub display device 51 is implemented by a touch panel, the user may input a control command by touching the sub display unit 51.

The main display unit 60 may display an ultrasound image and information related to an operation of the ultrasonic imaging apparatus 1. For example, the main display unit 60 may display a volume image of fetus or an image about a reference plane extracted from the volume image.

The main display unit 60 may include a plurality of display units 61 and 62, and the main display unit 61 and 62 may display different ultrasound images. For example, a first display unit 61 may display a volume image of fetus, and a second display unit 62 may display a plurality of reference plane images extracted from the volume image.

The display unit 61 and 62 may employ a display device, such as a Plasma Display Panel (PDP), a Liquid Crystal Display (LCD), a Light Emitting Diodes (LED), an Organic Light Emitting Diodes (OLED), or an Active Matrix Organic Light Emitting Diodes (AMOLED).

The ultrasonic imaging apparatus 1 may include a communication unit 120, a storage 130, and a processor 200.

The communication unit 120 may communicate with an external device and a server via a network 3. The communication unit 120 may transmit/receive data to/from a hospital server 4 or another medical apparatus 5 in the same hospital connected by Picture Archiving and Communication System (PACS). The communication unit 120 may communicate data according to Digital Imaging and Communications in Medicine (DICOM).

Particularly, the communication unit 120 may transmit/receive data related to diagnosis of an object, such as an ultrasound image, an ultrasound data, and a Doppler data of the object 1 via the network 3, and also may transmit/receive a medical image, such as a CT image, a MRI image, acquired by other medical apparatus 5. Further, the communication unit 120 may receive information about diagnostic history and treatment schedule of patients from the server 4 and may use for the diagnosis of the object 1. The communication unit 120 may perform data communication with a portable terminal 6 of a doctor or a patient as well as the hospital server 4 and the medical apparatus 5 provided in the hospital.

The communication unit 120 may send/receive data to/from the hospital server 4, the medical apparatus 5 or the portable terminal 6 by being connected to the network 3 via a wire or a wireless communication. The communication unit 120 may include one or more component, e.g., a local area communication module 121, a wired communication module 122, and a mobile communication module 123, to allow communication with an external device.

The local area communication module 121 may represent a module for local area communication within a certain distance. A local area communication technology according to an embodiment of the present disclosure may include Wireless LAN, Wi-Fi, Bluetooth, zigbee, Wi-Fi Direct (WFD), ultra wideband (UWB), Infrared Data Association (IrDA), Bluetooth Low Energy (BLE), Near Field Communication (NFC), but is not limited thereto.

The wired communication module 122 may represent a module for a communication by using an electric signal or an optical signal. A wired communication technology according to an embodiment of the present disclosure may include a pair cable, a coaxial cable, a fiber optic cable, and an Ethernet cable.

The mobile communication module 123 may transmit/receive a radio signal to/from at least one of a base station, an external terminal and a server on the mobile communication network. The radio signal may include a voice call signal, a video communication call signal or data which is various according to transmission/reception of text/multimedia message.

The storage 130 may store various information needed for operations of the ultrasonic imaging apparatus 1. For example, the storage 130 may store an operation system of the ultrasonic imaging apparatus 1, and an application needed for operations of the ultrasonic imaging apparatus 1.

The storage 130 may store data generated by the operation of the ultrasonic imaging apparatus 1. For example, the storage 130 may store volume data outputted from the data acquisition unit 110, and volume images generated based on the volume data. In addition, the storage 130 may store an image corresponding to a reference plane extracted from the volume data.

The storage 130 may include high-speed random access memory, magnetic disk, SRAM, DRAM, or ROM but is not limited thereto.

The storage 130 may be detachably installed on the ultrasonic imaging apparatus 1. For example, the storage 130 may include Compact Flash (CF) Card, Secure Digital (SD) Card, Smart Media (SM) Card, Multimedia Card (MMC), or Memory Stick, but is not limited thereto.

The processor 200 may generally control operations of the ultrasonic imaging apparatus 1. Particularly, the processor 200 may control operations of the display unit 60, the manipulation panel 50, the communication unit 120, the storage 130 and the data acquisition unit 110 according to a control command, which is inputted through the manipulation panel 50.

The processor 200 may be implemented by array of multiple logic gates, a combination with universal microprocessors 200 and memory in which programs implemented in the microprocessors 200 are stored. For example, the processor 200 may be implemented as a central processing unit (CPU) and a graphic processing unit (GPU), but is not limited thereto.

The processor 200 may generate a volume image based on a volume data. The processor 200 may generate an ultrasound image by a scan conversion process of a volume data. The ultrasound image generated in the process 200 may include an Amplitude mode (A mode), a Brightness mode (B mode), a Doppler mode (D mode), an Elastography mode (E mode), and a Motion mode (M mode), but is not limited thereto.

The processor 200 may generate a plurality of 2D ultrasound images, and 3D volume images by applying data interpolation to the 2D ultrasound images.

The processor 200 may perform pre-process of volume data before generating a volume image. For example, the pre-processing configured to remove a noise included in the volume data, and configured to normalize a volume data may be performed.

The processor 200 may extract a certain reference plane from a volume data outputted from the data acquisition unit 110, and may generate a cross-sectional image corresponding to the reference plane.

The reference plane may be a certain cross-section of an object, and may represent a cross-section where test items needed for the diagnosis of an object are prominently displayed. The test items needed for the diagnosis of the object may be different depending on a diagnostic region and a diagnostic target, and the reference plane may also be determined depending on a diagnostic region and a diagnostic target. Hereinafter a reference plane used for the diagnosis of fetal head will be described.

Figure 4:
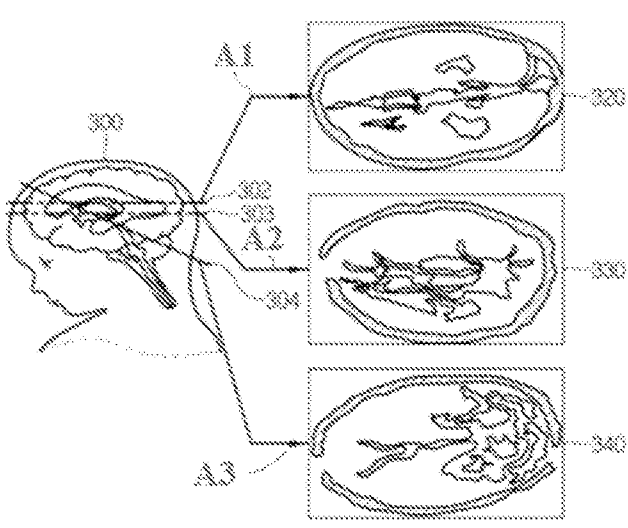

FIGS. 3 and 4 are views schematically illustrating an image of a reference plane of fetus, FIG. 3 schematically illustrates a mid-sagittal plane, and FIG. 4 schematically illustrates a cross section.

In order to diagnose a fetal head, test items, such as biparietal diameter (BPD), occipitofrontal diameter (OFD), head circumference (HC) of fetal head 300, Posterior Cerebral Ventricle Diameter (Vp), abdominal circumference (AC), femur length (FL), femur length (FL), a location of thalamus (T), Doppler information of vessels, Transverse cerebellar Diameter (TCD), and Cisterna Magna (CM) may be needed.

A reference plane for the diagnosis of fetal head 300 may be at least one of a Mid Sagittal Plane (MSP) 310, a Trans-Ventricular Plane (TVP) 320, a Trans-Thalamic Plane (TTP) 330, and a Trans-Cerebellar Plane (TCP) 340, as illustrated in FIGS. 3 and 4.

As illustrated in FIG. 3, among sagittal planes, the Mid Sagittal Plane (MSP) 310 may represent a plane corresponding to a line segment 301 dividing a center of the fetal head 300. The Mid Sagittal Plane (MSP) 310 may be used to detect the Trans-Ventricular Plane (TVP) 320, the Trans-Thalamic Plane (TTP) 330, and the Trans-Cerebellar Plane (TCP) 340, but is not limited thereto.

As illustrated in FIG. 4, among axial planes of the fetal head 300, the Trans-Ventricular Plane (TVP) 320 may represent a plane corresponding to a line segment 302 passing through ventricle, the Trans-Thalamic Plane (TTP) 330 may represent a plane corresponding to a line segment 303 passing through thalamus, and the Trans-Cerebellar Plane (TCP) 340 may represent a plane corresponding to a line segment 304 passing through cerebellum.

The Trans-Thalamic Plane (TTP) 330 may be used to measure test items, such as head circumference (HC) of fetal head 300, biparietal diameter (BPD) and occipitofrontal diameter (OFD). The Trans-Cerebellar Plane (TCP) 340 may be used to measure test items, such as Transverse cerebellar Diameter (TCD), and Cisterna Magna (CM). The Trans-Ventricular Plane (TVP) 320 may be used to measure test items, such as Posterior Cerebral Ventricle Diameter (Vp).

That is, to accurately diagnose the object, a reference plane in which test items are displayed may be needed to be accurately extracted. The processor 200 may determine whether the acquisition position of a volume data is within a predetermined allowable range before extracting a reference plane.

The predetermined allowable range may represent a location which is appropriate to extract a plurality of reference planes, and may be defined based on a relationship between a plurality of reference planes.

Figure 5:
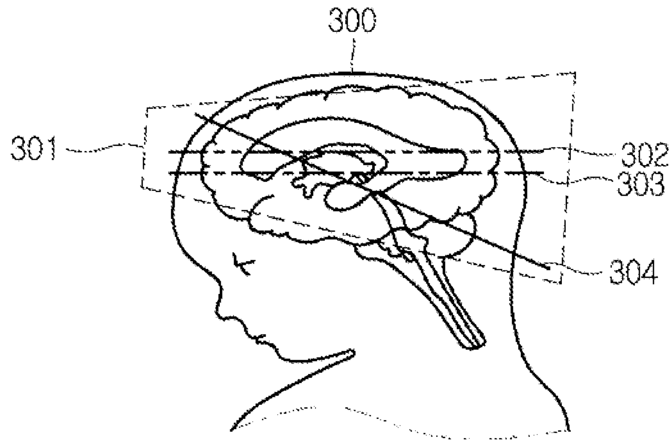
FIG. 5 is a view schematically illustrating an example of an allowable range.

FIG. 5 is a view schematically illustrating an example of an allowable range and FIGS. 6A-6D are views schematically illustrating an example of landmark information.

Referring to FIGS. 4 and 5, when an object is fetal head 300, an allowable range 301 may be defined to include the Trans-Ventricular Plane (TVP) 320 and the Trans-Cerebellar Plane (TCP) 340.

The line segment 303 passing through thalamus corresponding to the Trans-Thalamic Plane (TTP) 330 may be placed between the line segment 302 passing through ventricle corresponding to the Trans-Ventricular Plane (TVP) 320 and the line segment 304 passing through cerebellum corresponding to the Trans-Cerebellar Plane (TCP) 340. The Mid Sagittal Plane (MSP) 310 may have an orthogonal relationship with the Trans-Ventricular Plane (TVP) 320 and the Trans-Cerebellar Plane (TCP) 340, and thus when the allowable range is defined as the Trans-Ventricular Plane (TVP) 320 and the Trans-Cerebellar Plane (TCP) 340, all kinds of reference planes may be extracted.

In addition, since a reference plane is well known to a user and the reference plane is a location where an ultrasound signal is accurately acquired, scanning of fetal brain may be easily performed by setting the allowable range 301 to include the plurality of reference planes. In other words, the allowable range 301 may include at least two reference planes among the plurality of reference planes.

The processor 200 may determine whether the acquisition position of the volume data, which is acquired by using pre-stored landmark information, is within the allowable range.

The pre-stored landmark information may represent information about landmark indicating anatomical features of an object, that is landmark information may include anatomical features of Cavum septum pellucidum (CSP), Cerebellum, Choroid plexus, Lateral ventricle, Cisterna magna, and Thalami.

Particularly, the landmark information may be a certain cross-section of an object. That is, the landmark information may include information, e.g., a shape, a size, and a location of a landmark, which are existed in the certain cross-section, and a correlation with another landmark.

There may be no limitation to a cross-section of an object, which is to be landmark information, but as illustrated in FIGS. 6A-6D, landmark information may be related to a reference plane indicating anatomical features of an object clearly.

Figure 6A:
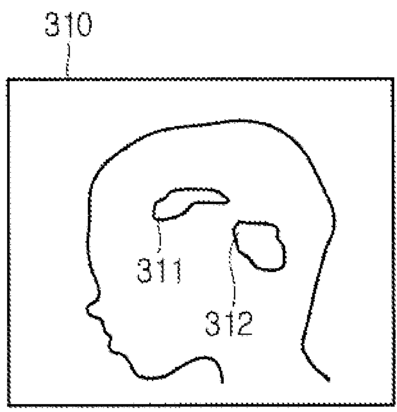
FIGS. 6A-6D are views schematically illustrating an example of landmark information.
Figure 6B:
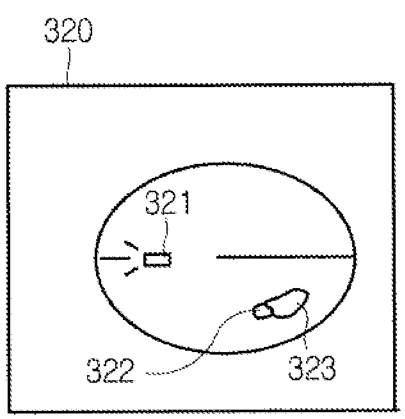
Figure 6C:
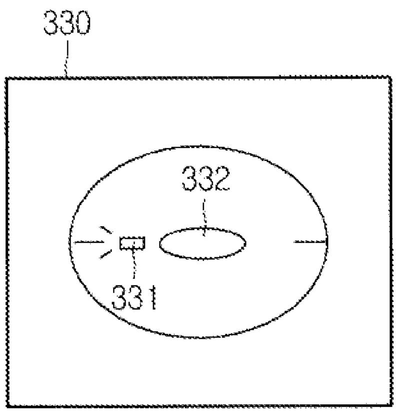
Figure 6D:
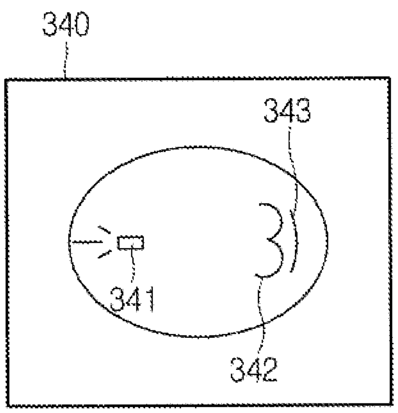

Particularly, the landmark information may include at least one of landmark information about the Mid Sagittal Plane (MSP) 310, as illustrated in FIG. 6A, landmark information about the Trans-Ventricular Plane (TVP) 320, as illustrated in FIG. 6B, landmark information about the Trans-Thalamic Plane (TTP) 330, as illustrated in FIG. 6C, and landmark information about the Trans-Cerebellar Plane (TCP) 340, as illustrated in FIG. 6D.

Landmark information about each plane may include landmark commonly existed in the plurality of reference planes and landmark distinctively existed on a single reference plane.

As illustrated in FIGS. 6A-6D, landmark information may include Cavum septum pellucidum (CSP), which is commonly existed on each reference plane, as common landmarks 311, 321, 331, and 341. However, the shape, the size, the position of the Cavum septum pellucidum (CSP) may vary according to the reference plane.

In addition, the Mid Sagittal Plane (MSP) 310 may include the Cerebellum 312 as a distinctive landmark, and the Trans-Ventricular Plane (TVP) 320 may include the lateral ventricle 323 and the choroid plexus 322 as a distinctive landmark, the Trans-Thalamic Plane (TTP) 330 may include the Thalami 332 as a distinctive landmark, and the Trans-Cerebellar Plane (TCP) 340 may include the Cerebellum 342 and the cisterna magna 343 as a distinctive landmark.

The acquisition position of the volume data may be determined based on the landmark information. Particularly, the processor 200 may extract at least one sample plane from the volume data, may determine whether an acquisition position of a volume data is within an allowable range by comparing a similarity between landmark of the sample plane and landmark information of pre-stored reference plane, and may extract a reference plane of the volume data when the acquisition position of the volume data is within an allowable range. Hereinafter the extraction of the reference plane by using landmark information will be described in detail.

Figure 7:
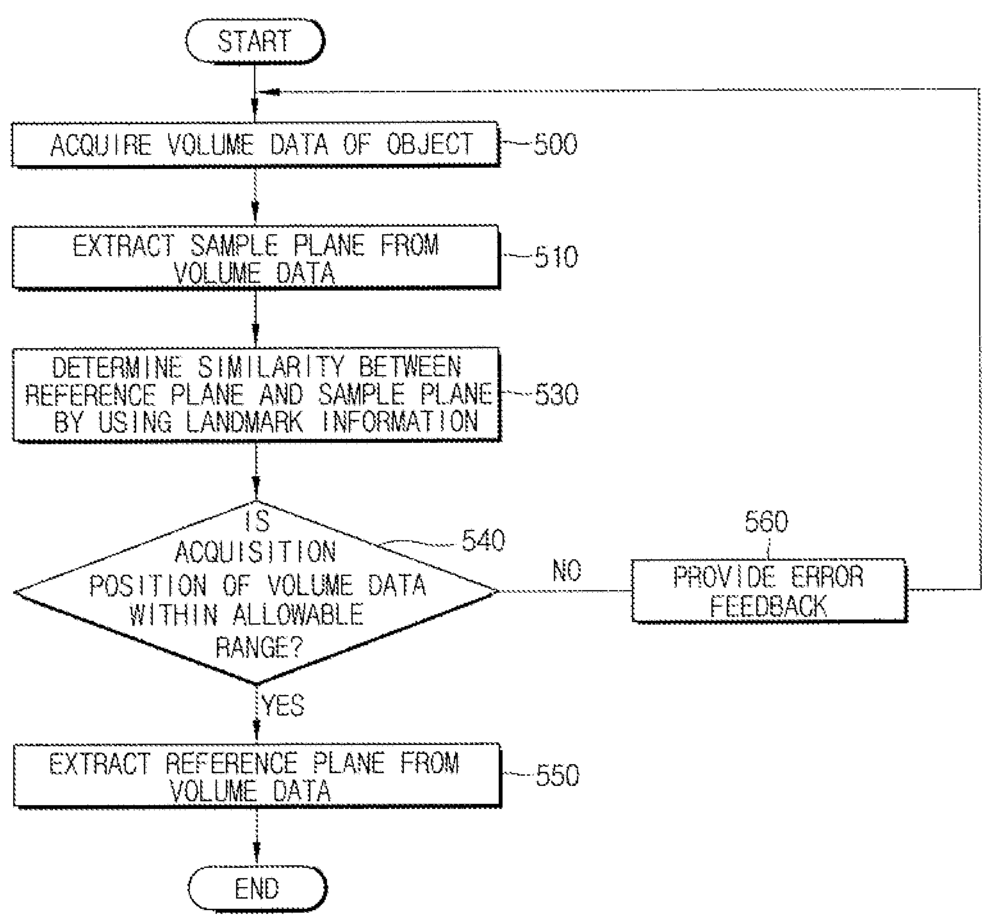
FIG. 7 is a flowchart illustrating an example of a method of extracting reference plane by an ultrasonic imaging apparatus according to an embodiment of the present disclosure.
Figure 8:
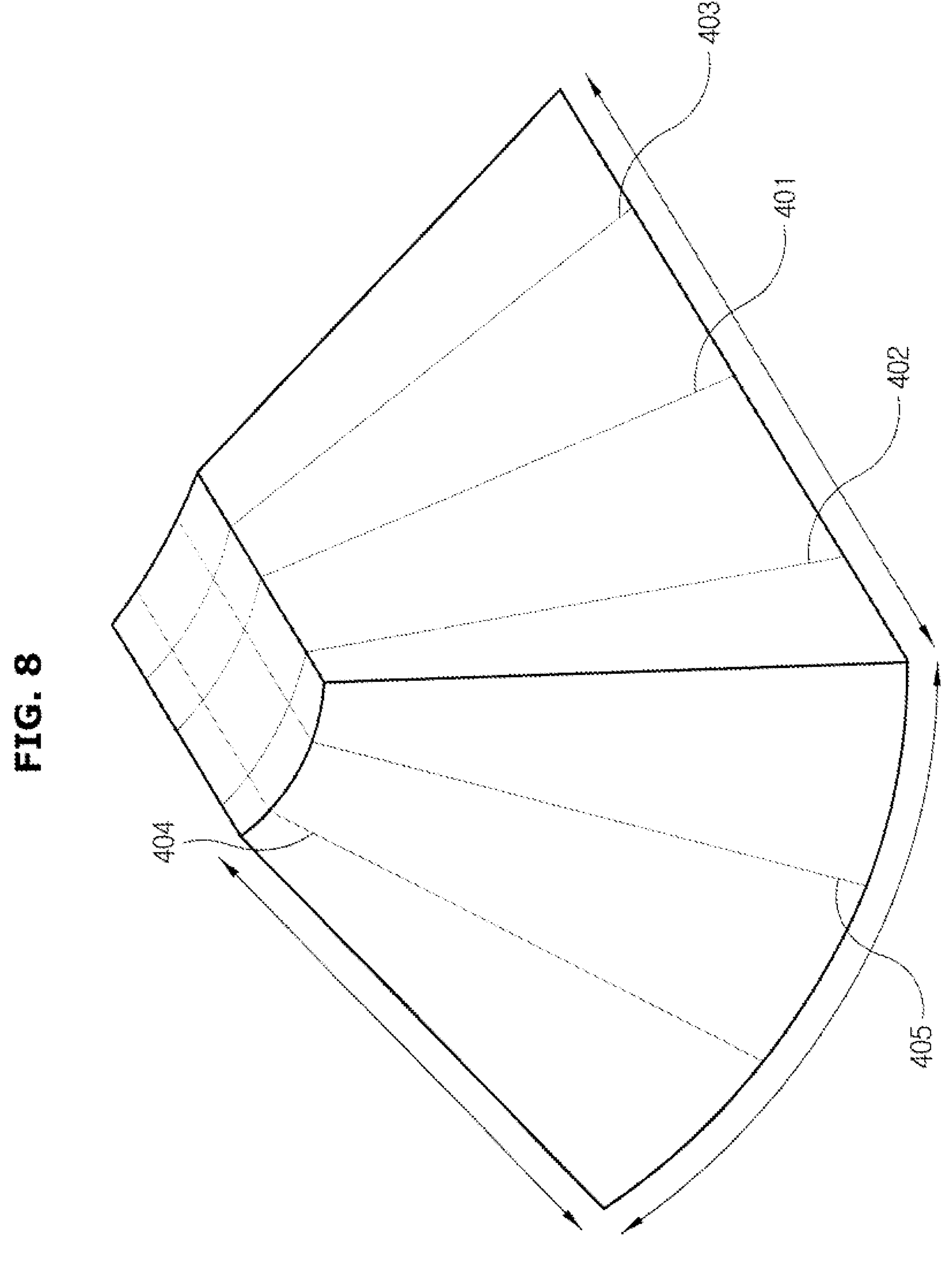
FIG. 8 is a view illustrating a sample plane extracted from a volume data.

FIG. 7 is a flowchart illustrating an example of a method of extracting a reference plane by an ultrasonic imaging apparatus according to an embodiment of the present disclosure and FIG. 8 is a view illustrating a sample plane extracted from a volume data.

Referring to FIG. 7, the ultrasonic imaging apparatus 1 may acquire a volume data of an object (510), and may extract a sample plane from the volume data (520). The sample plane may represent a cross-section extracted from the volume data, and thus a plurality of the sample planes 401, 402, 403, 404 and 405 may be extracted from the volume data, as illustrated in FIG. 8.

Among the volume data, a plane where features are remarkably illustrated may be extracted as the sample plane 401, 402, 403, 404 and 405. For example, the processor 200 may extract a plane where the difference of brightness is remarkably displayed, or a plane having pre-determined brightness value from the volume data as the sample planes 401, 402, 403, 404 and 405.

The ultrasonic imaging apparatus 1 may determine a similarity between the reference plane and the sample planes 401, 402, 403, 404 and 405 by using landmark information (530). As mentioned above, since the landmark information may include landmark about the reference plane, the processor 200 may compare the sample planes 401, 402, 403, 404 and 405 and the reference plane by using landmark information.

Particularly, the processor 200 may detect an outline in the sample planes 401, 402, 403, 404 and 405. The outline may be detected through an edge mask, such as Sobel mask, Prewitt mask, Robert mask, Canny mask, but is not limited thereto.

The processor 200 may sequentially determine a similarity between each sample plane 401, 402, 403, 404 and 405 and the reference plane by comparing an outline detected in the sample planes 401, 402, 403, 404 and 405 with landmark corresponding to the reference plane. The processor 200 may determine the similarity between each sample plane 401, 402, 403, 404 and 405 and the reference plane by performing conversion of scale on the landmark corresponding to the reference plane or by rotating the landmark corresponding to the reference plane.

At this time, the landmark information may be related to a plane corresponding to a plane used to define an allowable range. For example, when the allowable range is defined as the Trans-Ventricular Plane (TVP) 320 and the Trans-Cerebellar Plane (TCP) 340, landmark information may include a landmark about Trans-Ventricular Plane (TVP), as illustrated in FIG. 6B, and a landmark about Trans-Cerebellar Plane (TCP), as illustrated in FIG. 6D. In addition, the processor 200 may compare a plurality of extracted planes 401, 402, 403, 404 and 405 with landmark about the Trans-Ventricular Plane (TVP) 320, and then may determine a similarity between each extracted plane 401, 402, 403, 404 and 405 and the Trans-Ventricular Plane (TVP) 320. The processor 200 may compare a plurality of extracted planes 401, 402, 403, 404 and 405 with landmark about the Trans-Cerebellar Plane (TCP) 340, and then may determine a similarity between each extracted plane 401, 402, 403, 404 and 405 and Trans-Cerebellar Plane (TCP) 340.

The ultrasonic imaging apparatus 1 may determine whether the acquisition position of the volume data is within the allowable range based on the similarity (540). Particularly, the processor 200 may determine whether the acquisition position is within an allowable range according to the presence of an extracted plane in which a similarity with the reference plane is higher than a threshold, and according to the number of an extracted plane in which a similarity is higher than a threshold.

For example, when an extracted plane having a similarity more than the threshold with a landmark about the Trans-Ventricular Plane (TVP) 320 of FIG. 6B, and an extracted plane having a similarity more than the threshold with a landmark about the Trans-Cerebellar Plane (TCP) 340 of FIG. 6D are existed, the acquisition position of the volume data may be determined to be within an allowable range.

When the acquisition position of the volume data is determined to be within the allowable range (YES of 540), the ultrasonic imaging apparatus 1 may extract a plurality of reference planes from the volume data. For the extraction of the reference plane, information related to a similarity between the extracted plane determined in step 530 and the reference plane may be used.

In addition, for the extraction of the reference plane, landmark information about the aforementioned reference plane may be used. Particularly, the processor 200 may extract a plane having a highest similarity with a landmark corresponding to a reference plane, as a reference plane, by searching an extracted plane having a high similarity with a reference plane and an adjacent plane. In addition, the processor 200 may extract another reference plane from a single reference plane based on an anatomical relationship between a plurality of reference planes.

For example, when a first extracted plane 401 has a high similarity with the Trans-Ventricular Plane (TVP) 320, that is a reference plane, the processor 200 may extract the Trans-Ventricular Plane (TVP) 320 of the object by searching a plane corresponding to the Trans-Ventricular Plane (TVP) 320 in a position adjacent to the first extracted plane 401. At this time, when the Trans-Ventricular Plane (TVP) 320 is extracted, landmark information about the Trans-Ventricular Plane (TVP) 320 may be used.

When the Trans-Ventricular Plane (TVP) 320 is detected, the processor 200 may extract the Trans-Cerebellar Plane (TCP) 340 in a position which is rotated by a certain angle with respect to Cavum septum pellucidum (CSP), which is a common landmark existed in the reference plane, and may extract a plane crossing Cavum septum pellucidum (CSP) while being perpendicular to the Trans-Ventricular Plane (TVP) 320, as the Mid Sagittal Plane (MSP) 310.

Meanwhile, when a similarity between the sample plane and the reference plane is equal to or lower than a threshold (NO of 540), the ultrasonic imaging apparatus 1 may provide an error feedback and then return to step 510.

By determining whether the acquisition position of the volume data is within the allowable arrange prior to extracting a reference plane, load of the extraction of the reference plane may be reduced. In addition, a plurality of reference planes is automatically extracted from the volume data by using pre-stored landmark information so that a user may easily diagnose fetus.

Meanwhile, since there are difficulties in directly observing fetus, and a position and a posture of fetus are changed as time passes, it may be difficult for a user to determine whether an acquisition position of a volume data is within an allowable range. The processor 200 may provide feedback to a user according to the acquisition position of the volume data. Hereafter a method of providing feedback according to the acquisition position of the volume data will be described in detail.

Figure 9:
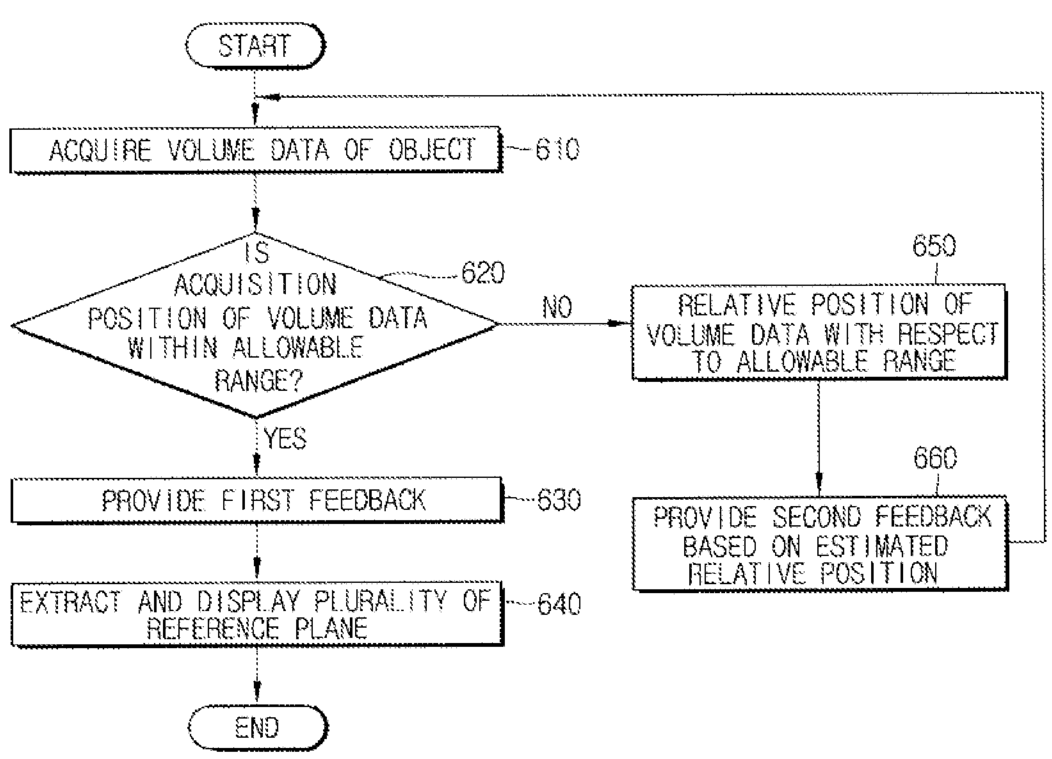
FIG. 9 is a flowchart illustrating an example of a method of providing feedback of an ultrasonic imaging apparatus according to an embodiment of the present disclosure.
Figure 10A:
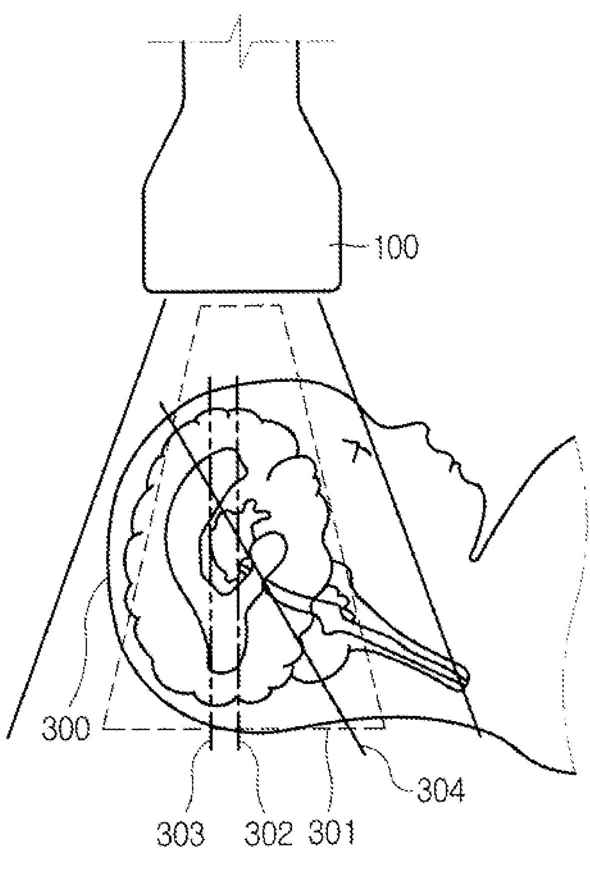
FIGS. 10A-10C are views schematically illustrating a relation between a volume data and an allowable range.
Figure 10B:
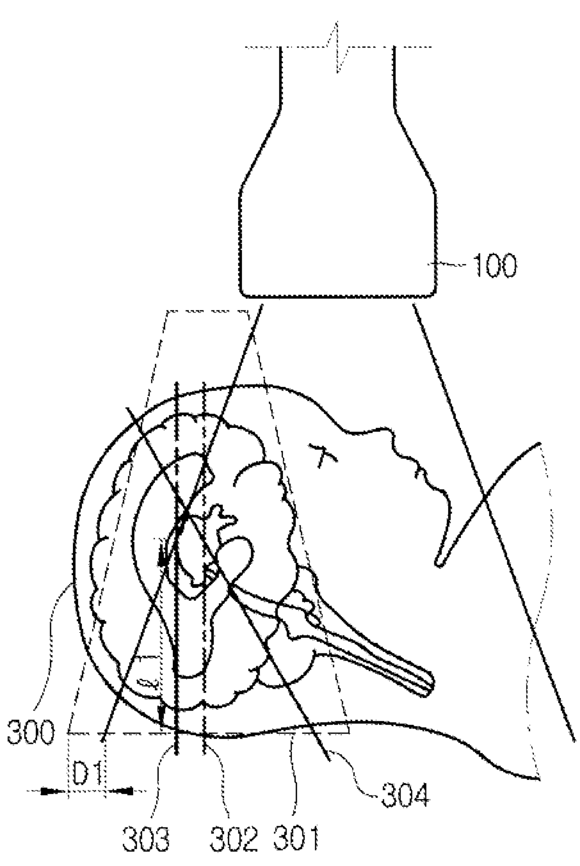
Figure 10C:
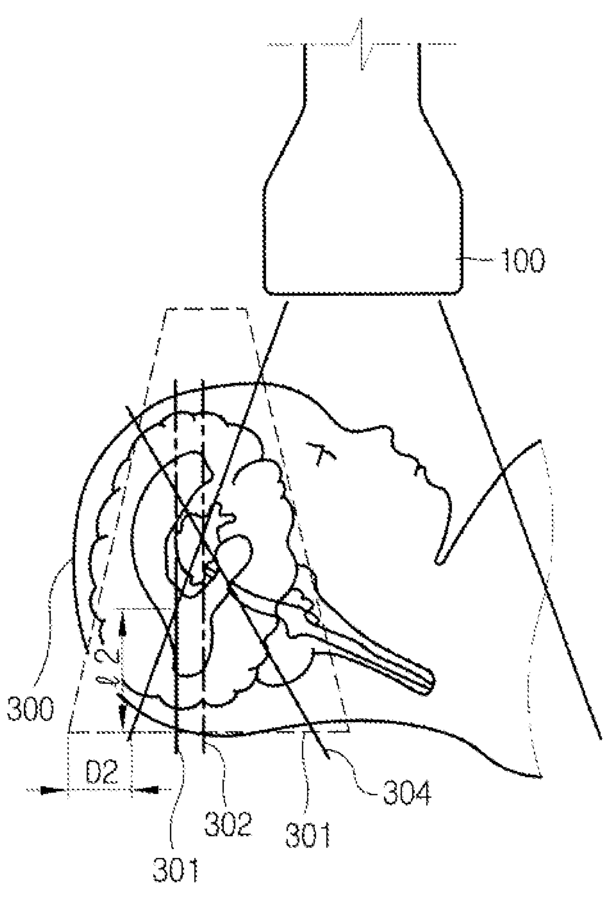

FIG. 9 is a flowchart illustrating an example of a method of providing feedback of an ultrasonic imaging apparatus according to an embodiment of the present disclosure and FIGS. 10A-10C are views schematically illustrating a relation between a volume data and an allowable range.

Referring to FIG. 9, the ultrasonic imaging apparatus 1 may acquire a volume data (610). The ultrasonic imaging apparatus 1 may determine whether an acquisition position of the volume data is within an allowable range (620). As mentioned in FIG. 7, whether the acquisition position of the volume data is within the allowable range may be determined by comparing a sample plane of the volume data with the pre-stored landmark information, but is not limited thereto.

When the acquisition position of the volume data is within the allowable range (YES of 620), the ultrasonic imaging apparatus 1 may provide a first feedback (630), may extract a plurality of reference planes, and then may display the extracted reference plane (640). Particularly, as illustrated in FIG. 10A, when the volume data acquired by the ultrasonic probe 100 includes the allowable range, by providing the first feedback, it will be informed to a user that the position of the ultrasonic probe 100 is appropriate.

The first feedback may be provided in a tactile, an acoustic and visual manner. For example, the processor 200 may control the ultrasonic probe 100 to generate a pre-set haptic, may control the main display unit 60 or the sub display unit 51 to display a pre-set screen, or may control a speaker provided on the ultrasonic imaging apparatus 1 to generate a pre-set sound.

When the acquisition position of the volume data is not within the allowable range (NO of 620) the ultrasonic imaging apparatus 1 may estimate a relative position of the volume data with respect to the allowable range (650). The processor 200 may estimate the relative position of the volume data based on a similarity between a sample plane extracted from the volume data and a pre-stored landmark.

As illustrated in FIG. 10B, when a relative position between an allowable range and the volume data is D1, I1 of the reference plane may be existed in the volume data, and as illustrated in FIG. 10C, when a relative position between an allowable range and the volume data is D2 (D2>D1), I2 of the reference plane may be existed in the volume data. In other words, as the acquisition position of the volume data is far from the allowable range, the similarity between the sample plane and the pre-stored landmark may be lowered. Therefore, the processor 200 may estimate a relative distance between the acquisition position of the volume data and the allowable range according to the similarity between the sample plane and the pre-stored landmark.

The ultrasonic imaging apparatus 1 may provide a second feedback based on the estimated relative position (660), and then return to a step 610. The second feedback may be provided in a tactile, an acoustic and visual manner, as like the first feedback, but the second feedback may be provided differently from the first feedback to avoid confusion with the first feedback. For example, the second feedback may provide a haptic having different from the haptic of the first feedback.

In addition, the processor 200 may differently provide the second feedback according to the estimated relative position. For example, as the relative position is closer, the size of the generated haptic may be reduced, and as the relative position is far, the size of the generated haptic may be increased. In addition, the processor 200 may control the display unit 60 or the sub display unit 51 so that the second feedback is displayed to be small and blur as the relative position is closer, and the second feedback is displayed to be big and clear as the relative position is far.

A different feedback from each other may be provided according to the acquisition position of the volume data so that a user may easily acquire the volume data corresponding to the allowable range.

Figure 11:
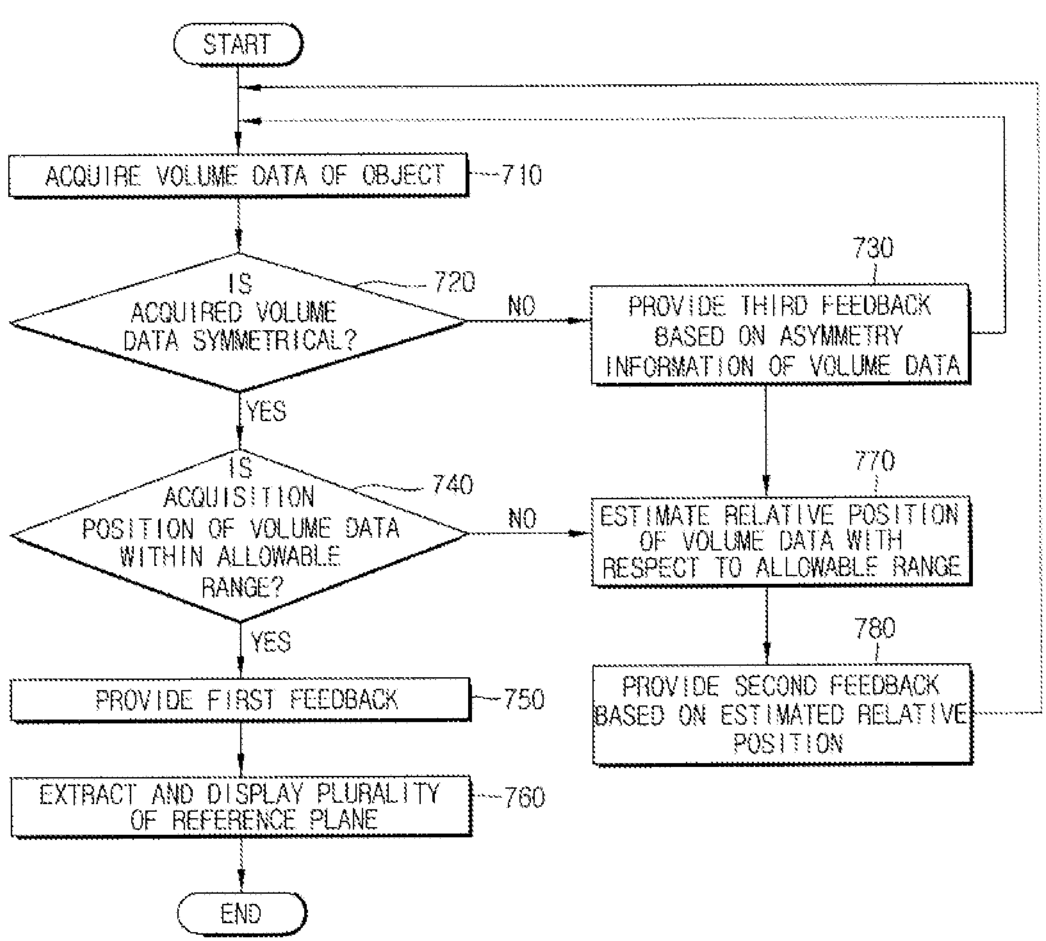
FIG. 11 is a flow chart illustrating another method of a method of providing feedback of an ultrasonic imaging apparatus according to an embodiment of the present disclosure.
Figure 12A:
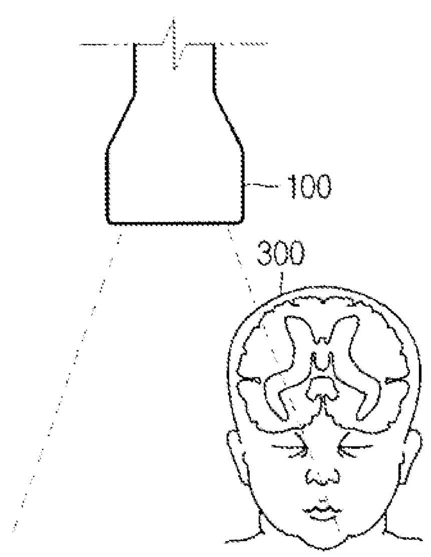
FIGS. 12A-12C are views schematically illustrating the symmetry of a volume data.
Figure 12B:
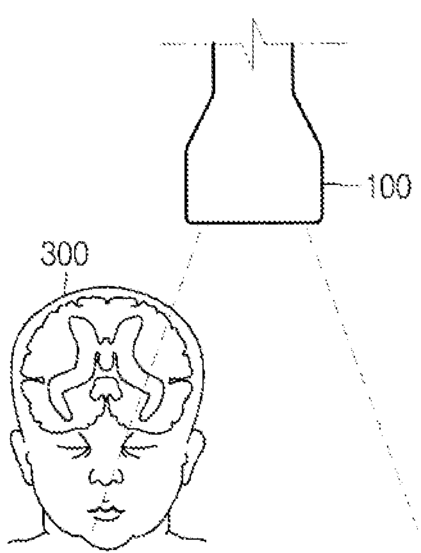
Figure 12C:
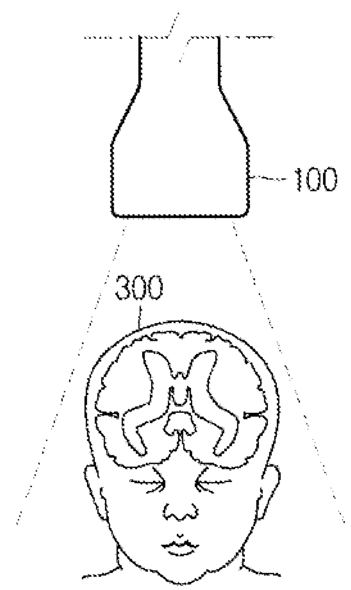

FIG. 11 is a flow chart illustrating another method of a method of providing feedback of an ultrasonic imaging apparatus according to an embodiment of the present disclosure and FIGS. 12A-12C are views schematically illustrating the symmetry of a volume data.

Referring to FIG. 11, the ultrasonic imaging apparatus 1 may acquire a volume data (710). The ultrasonic imaging apparatus 1 may determine whether the acquired volume data is symmetrical (720). The processor 200 may determine whether the object is asymmetrically placed on an edge of the volume data, as illustrated in FIGS. 12A and 12B or whether the object is symmetrically placed on the center of the volume data, as illustrated in FIG. 12C.

Particularly, the processor 200 may extract at least one plane from the volume data, and may determine whether the volume data is symmetrically by determining the symmetry of the extracted plane. At this time, the extracted plane may be the same as the aforementioned sample plane, but is not limited thereto.

When the volume data is asymmetrical (NO of 720) the ultrasonic imaging apparatus 1 may provide a third feedback based on asymmetry information of the volume data (730). The third feedback may be provided in a tactile, an acoustic and visual manner, as like the first feedback, but the third feedback may be provided differently from the first and second feedback to avoid confusion with the first and second feedback.

The third feedback may be provided in a different manner according to the direction of the asymmetry. Particularly, a feedback in a case in which the object is placed in the position of FIG. 12A, and a feedback in a case in which the object is placed in the position of FIG. 12B may be different.

When the volume data is symmetrical, the ultrasonic imaging apparatus 1 may determine whether the acquisition position of the volume data is within the allowable range (740).

When the acquisition position of the volume data is within the allowable range (YES of 740), the ultrasonic imaging apparatus 1 may provide the first feedback (750), and may extract and display a plurality of reference planes (760)

When the acquisition position of the volume data is out of the allowable range (NO of 740), the ultrasonic imaging apparatus 1 may estimate a relative position of the volume data with respect to the allowable range (770), may provide the second feedback based on the estimated relative position (780), and may return to a step 710.

According to an embodiment of the disclosure, the processor 200 may estimate a position of the ultrasonic probe 100 by using an ultrasound image. Also, according to an embodiment of the disclosure, the processor 200 may estimate a position of the ultrasonic probe 100 and an orientation of the ultrasonic probe 100 by using the ultrasound image. According to an embodiment of the disclosure, the processor 200 may estimate a position of the ultrasonic probe 100 and an orientation of the ultrasonic probe 100 based on type and arrangement of anatomical features recognized in the ultrasound image.

Also, according to an embodiment of the disclosure, the processor 200 may estimate a position of the ultrasonic probe 100 and an orientation of the ultrasonic probe 100 by using an artificial intelligence (AI) model. The processor 200 may input the ultrasound image into the AI model. The AI model may output the estimated position and the estimated orientation of the ultrasonic probe 100.

The processor 200 may display the estimated position of the ultrasonic probe 100 on a pictogram or a scout view. The pictogram or the scout view may represent a shape of the object. The pictogram or the scout view may represent a simplified shape of the object. The processor 200 may display the position of the ultrasonic probe 100 by locating an indicator corresponding to the ultrasonic probe 100 on the estimated position of the ultrasonic probe 100 on the pictogram.

Also, the processor 200 may display the estimated orientation of the ultrasonic probe 100. Unlike FIG. 1, the ultrasonic imaging apparatus 1 may be implemented by a portable ultrasonic apparatus configured to be hand-held when moving at a long distance. The portable ultrasonic apparatus 1 may be a PACS viewer, a smart phone, a lap top computer, a personal digital assistant (PDA), and a tablet personal computer, but is not limited thereto.

In addition, FIG. 1 illustrates that the ultrasonic probe 100 is implemented by a wired probe, but is not limited thereto. For example, the ultrasonic probe 100 may be implemented by a wireless probe.

In FIGS. 4 to 12, fetal head is illustrated as an object, but an object is not limited thereto.

Figure 13:
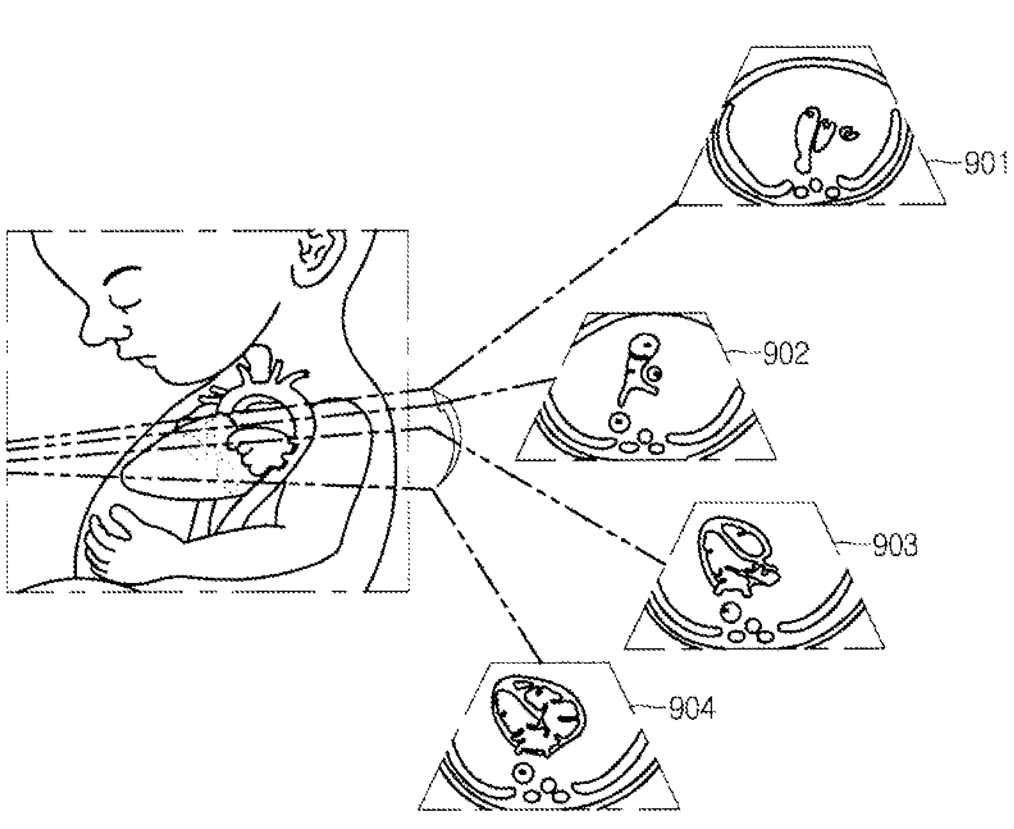
FIG. 13 is a view schematically illustrating a reference plane when an object is a heart.
Figure 14:
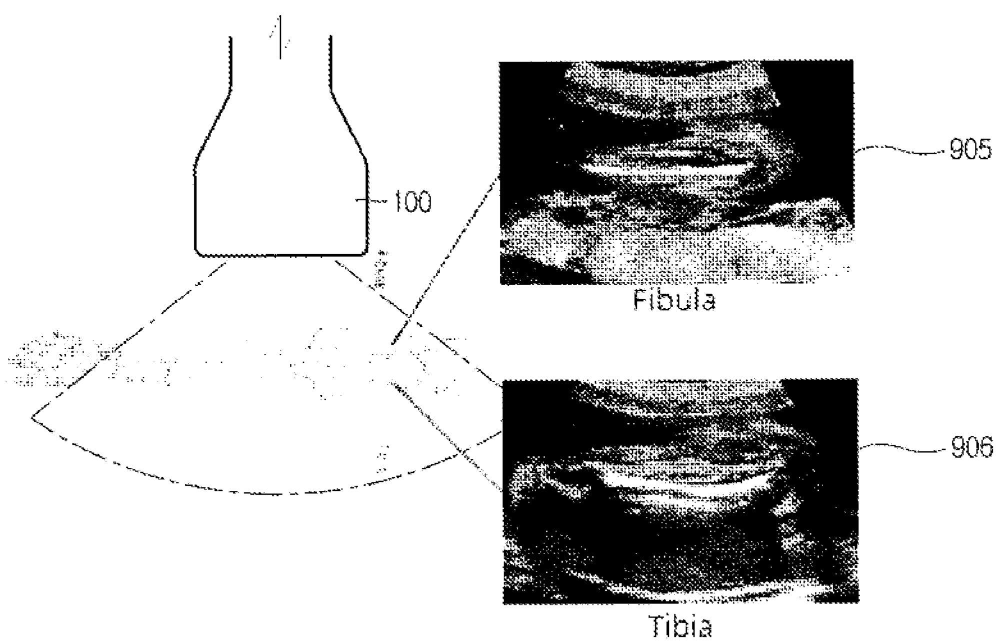
FIG. 14 is a view schematically illustrating a reference plane when an object is legs.

FIG. 13 is a view schematically illustrating a reference plane when an object is a heart and FIG. 14 is a view schematically illustrating a reference plane when an object is legs.

The object may be a fetal heart, as illustrated in FIG. 13. When the object is the fetal heart, a reference plane may be three vessel view (3VT), Right ventricular outflow tract (RVOT), and Four-chamber view, and fetal atrium and fetal ventricles may be used as landmark information.

In addition, the object may be fetal legs, as illustrated in FIG. 14. When the object is fetal legs, a cross-section of fibula or a cross-section of tibia may be a reference plane, and fibula and tibia may be used landmark information.

According to an embodiment of the disclosure, the processor 200 may acquire a reference plane image including at least a part of landmarks. The processor 200 may acquire a reference plane image based on a capture signal (e.g.: freeze signal) input by a user. If a user indicate the captured ultrasound image as a first reference plane, the processor 200 may store the ultrasound image as a reference plane image of the first reference plane.

According to an embodiment of the disclosure, the processor 200 may automatically extract a reference plane image based on the similarity between the sample plane and the pre-stored landmark. If the similarity between the recognized object and the pre-stored landmark in the sample plane is greater than or equal to a reference value, the processor 200 may recognize the recognized object as the corresponding landmark. The processor 200 can automatically recognize the sample plane as a reference plane when more than a predetermined number or all of the landmarks included in the reference plane are recognized from the sample plane.

The storage 130 may store in advance a landmark list of a reference plane including at least one anatomical feature. The landmark list may include a list of anatomical features that should be included in the corresponding reference plane. For example, if the reference plane is a transcerebellar plane, a landmark list may include an anterior horns of the lateral ventricles, a CSP, a thalamus, a cerebellum, and a cisternal magna.

When the processor 200 acquires a reference plane, it may determine whether each anatomical feature in the landmark list corresponding to the obtained reference plane is included. The processor 200 may recognize each anatomical feature from the reference plane image and determine whether the reference plane image includes at least one anatomical feature in the landmark list.

According to an embodiment of the disclosure, the processor 200 may place indicators for anatomical features recognized in the reference plane image on the reference plane image. The recognized anatomical features are anatomical features included in the landmark list of a reference plane. The processor 200 may display the indicators on the reference plane image. For example, the processor 200 may place and display an indicator indicating a CSP recognized within the reference plane image on the region of the CSP in the reference plane image. According to an embodiment of the disclosure, an indicator indicating an anatomical feature may indicate the boundary of the anatomical feature shown in the reference plane image. Additionally, according to an embodiment of the disclosure, an indicator indicating an anatomical feature may indicate shading or color in a region corresponding to the anatomical feature in the reference plane image. Additionally, according to an embodiment of the disclosure, an indicator indicating an anatomical feature may correspond to text, an icon, or annotation placed around the anatomical feature in a reference plane image.

According to an embodiment of the disclosure, the processor 200 may display the extraction progress of the reference plane image. For example, the processor 200 may display a reference plane list according to the imaging protocol. The reference plane list may include at least one reference plane required to be acquired for the imaging protocol. The processor 200 may display information of whether acquisition of each of the at least one reference plane has been completed, thereby indicating the progress of extraction of the reference plane image.

According to an embodiment of the disclosure, an ultrasonic imaging apparatus 1 may receive a user input indicating information about anatomical features from a user. For example, the user may input text indicating the name of the anatomical feature using a keyboard, touch screen, touch pad, keys, mouse, or trackball included in the manipulation panel 50. Processor 200 may insert user input for the anatomical feature entered by the user into the ultrasound image. User input may be inserted as an annotation at a user-specified location (e.g., around an anatomical feature). User input may be inserted as pixel data on the ultrasound image or as text elements. According to an embodiment of the disclosure, the processor 200 may recognize an anatomical feature by recognizing an annotation input by a user. For example, when a user inserts the text "CSP" around CSP shown in the ultrasound image, the text may be inserted as pixel data on the ultrasound image. The processor 200 may recognize the pixel data corresponding to CSP as text information and recognize the CSP by using the text information. In this case, processor 200 may recognize the CSP only by recognizing the annotation without the process of recognizing the CSP from the ultrasound image.

Additionally, according to an embodiment of the disclosure, the processor 200 may generate and display an anatomical feature recognition result, which is information about whether each anatomical feature included in the landmark list has been recognized from the obtained reference plane image. The processor 200 may display the anatomical feature recognized from the reference plane image differently from the unrecognized anatomical feature in order to display the anatomical feature recognition result. According to an embodiment of the disclosure, the processor 200 may display all anatomical features included in the landmark list and display information about whether each anatomical feature has been recognized from the reference plane image. Information about the anatomical feature included in the landmark list can be expressed, for example, as text, an image representing the shape of the anatomical feature, or an icon, or a combination thereof.

According to an embodiment of the disclosure, the processor 200 may display the anatomical feature recognition result along with at least one of the ultrasound image or the reference plane image. The processor 200 may display the anatomical feature recognition result and at least one of the ultrasound image or the reference plane image in a single display view. For example, the processor 200 may display an ultrasound image or a reference plane image in a first area and display an anatomical feature recognition result in a second area that is different from the first area.

According to an embodiment of the disclosure, the processor 200 may display anatomical feature recognition results on an ultrasound image or a reference plane image. The processor 200 may display indicators of anatomical features recognized on the ultrasound image or a reference plane image. Additionally, the processor 200 may display information about anatomical features missing from the reference plane image on the reference plane image or in an area different from the area where the reference plane image is displayed.

According to an embodiment of the disclosure, the processor 200 may identify, acquire, or generate a reference plane image from an ultrasound image using an artificial intelligence (AI) model. The AI model may receive an ultrasound image as input, and output at least one reference plane image acquired from the receive ultrasound image. The AI model may acquire a reference plane image from an ultrasound image and generate a reference plane acquisition result. The processor 200 may save the acquired reference plane image. The reference plane acquisition result may indicate the type of reference plane image recognized in the ultrasound image.

According to an embodiment of the disclosure, the processor 200 may display a list of required reference planes, and display the obtained reference plane image at the location of the corresponding reference plane on the list as the reference plane acquisition result. The processor 200 may display a thumbnail of the acquired reference plane image on the list of required reference planes. The processor 200 may automatically recognize the reference plane image from ultrasound image data and update the newly recognized reference plane image on the reference plane list.

Additionally, according to an embodiment of the disclosure, the AI model may receive an ultrasound image as an input, recognize at least one anatomical feature corresponding to at least one landmark, and output an anatomical feature recognition result. Also, according to an embodiment of the disclosure, the AI model may receive an ultrasound image as input, and output a reference plane acquisition result and an anatomical feature recognition result. The reference plane acquisition result may indicate the type of reference plane image recognized in the ultrasound image. The anatomical feature recognition result may include information about the anatomical feature recognized in the reference plane image and information about the anatomical feature missing from the reference plane image.

According to an embodiment of the disclosure, the AI model may be provided in ultrasonic imaging apparatus 1 in on-device form. For example, processor 200 may perform the operation of an AI model.

Additionally, according to an embodiment of the present disclosure, the AI model may operate on an external server. The ultrasonic imaging apparatus 1 may transmit an ultrasound image to an external server and receive the reference plane acquistion result and the anatomical feature recognition result obtained from the AI model from the external server.

AI models may be implemented using various artificial neural network models or deep neural network models. Additionally, AI models may be learned and created using various machine learning algorithms or deep learning algorithms. The AI model may be implemented using, for example, a Convolutional Neural Network (CNN), Recurrent Neural Network (RNN), Generative Adversarial Network (GAN), or Long Short-Term Memory (LSTM).

The AI model may be learned using multiple ultrasound images, reference plane acquisition results, and anatomical feature recognition results.

According to an embodiment of the disclosure, the reference plane image may correspond to a pictogram. A pictogram is a picture that simplifies the shape of an object. Reference plane images may be simplified according to predetermined standards and expressed as pictograms. According to an embodiment of the present disclosure, the positions of a plurality of reference plane images are displayed in the pictogram, and the reference plane image may be displayed in the form of a thumbnail, icon, etc. at each position of the pictogram.

According to an embodiment of the disclosure, the processor 200 may display a pictogram which represents a shape of the object, and display the acquired reference plane image on the corresponding position of the pictogram. The processor 200 may display the acquired reference plane image on the pictogram as a thumbnail image.

The control method of the ultrasonic imaging apparatus 1 may be implemented as a computer readable code on a computer readable recording medium. The computer readable recording medium may include various kinds of recording medium in which data decipherable by the computer system is stored. For example, there may be a Read Only Memory (ROM), a Random Access Memory (RAM), a magnetic tape, a magnetic disk, a flash memory, and an optical data storage 130. In addition, the medium may be distributed to computer systems over a network, in which computer-readable code may be stored and executed in a distributed manner.

As is apparent from the above description, the ultrasound imaging apparatus and the control method thereof, the load of the extraction of the reference plane may be reduced by determining whether the acquisition position of the volume data is within the allowable range, prior to extracting the reference plane. In addition, the plurality of reference planes may be automatically extracted from the volume data by using pre-stored landmark information so that a user may easily diagnose a fetus.

In addition, the feedback may be provided to the user according to the acquisition position of the volume data so that the operation of the ultrasonic probe may be easily performed by the user.

Although a few embodiments of the present disclosure have been shown and described, it would be appreciated by those skilled in the art that changes may be made in these embodiments without departing from the principles and spirit of the disclosure, the scope of which is defined in the claims and their equivalents.

DESCRIPTION OF NUMERALS

1: ultrasonic imaging apparatus
100: ultrasonic probe
110: data acquisition unit
120: communication unit
130: storage
200: processor

What is claimed is:

1. An ultrasonic imaging apparatus comprising:
an ultrasonic probe;
a display; and
at least one processor configured to:
obtain ultrasound image data from the ultrasonic probe via a wired or wireless communication interface;
pre-store a landmark list that should be included in a reference plane,
wherein the landmark list includes at least one anatomical feature;
recognize, from the ultrasound image data, anatomical features that should be included in the landmark list based on a similarity between an object in the ultrasound image data and landmarks in the pre-stored landmark list;
automatically acquire the ultrasound image data as a reference plane image based on at least a predetermined number of the anatomical features being recognized from the ultrasound image data; and
display the acquired reference plane image on the display.

2. The ultrasonic imaging apparatus of claim 1, wherein the at least one processor is further configured to automatically acquire the reference plane image from the obtained ultrasound image data by using an AI (artificial intelligence) model.

3. The ultrasonic image apparatus of claim 2, wherein the at least one processor is further configured to perform an operation of the AI model.

4. The ultrasonic image apparatus of claim 1, wherein the at least one processor is further configured to recognize the at least one anatomical feature by using an AI model.

5. The ultrasonic image apparatus of claim 1, wherein the at least one processor is further configured to provide anatomical feature recognition result which represents whether each of the at least one anatomical feature included in the landmark list is detected in the acquired reference plane image,
wherein the landmark list of the reference plane comprises at least one anatomical feature which is required in the reference plane.

6. The ultrasonic image apparatus of claim 5, wherein the at least one processor is further configured to display the anatomical feature recognition result on the display.

7. The ultrasonic image apparatus of claim 5, wherein the at least one processor is further configured to display the anatomical feature recognition result along with at least one of the obtained ultrasound image data or the acquired reference plane image.

8. The ultrasonic image apparatus of claim 5, wherein the at least one processor is further configured to provide the anatomical feature recognition result by indicating a boundary of each of the recognized at least one anatomical feature on the reference plane image.

9. The ultrasonic image apparatus of claim 5, wherein the at least one processor is further configured to provide the anatomical feature recognition result by displaying shade or color overlaid on a region of each of the recognized at least one anatomical feature in the reference plane image.

10. The ultrasonic image apparatus of claim 5, wherein the at least one processor is further configured to provide the anatomical feature recognition result by displaying a list of the at least one anatomical feature included in the landmark list of the reference plane, and information of whether each of the at least one anatomical feature in the list is recognized in the acquired reference plane image.

11. The ultrasonic image apparatus of claim 1, wherein the at least one processor is further configured to display an anatomical feature indicator which indicates the recognized at least one anatomical feature.

12. The ultrasonic image apparatus of claim 11, wherein the anatomical feature indicator comprises at least one of a boundary of the recognized anatomical feature, shade or color overlaid on a region of the recognized anatomical feature in the reference plane image, text, annotation, or icon.

13. The ultrasonic image apparatus of claim 1, wherein the at least one processor is further configured to recognize the at least one anatomical feature by using text or annotation which is represented as a pixel data of the ultrasound image data.

14. The ultrasonic image apparatus of claim 1, wherein the at least one processor is further configured to provide reference plane acquisition result which represents whether the reference plane image included in a reference plane list is acquired, wherein the reference plane list comprises at least one reference plane required to be acquired.

15. The ultrasonic image apparatus of claim 14, wherein the at least one processor is further configured to display the reference plane list on the display, and display the reference plane acquisition result by displaying the acquired at least one reference plane image on the displayed reference plane list.

16. The ultrasonic image apparatus of claim 15, wherein the at least one processor is further configured to, if a new reference plane image is acquired, update the displayed reference plane acquisition result by adding the acquired new reference plane image to the displayed reference plane list.

17. The ultrasonic image apparatus of claim 1, wherein the at least one processor is further configured to display a pictogram which represents a shape of the object, and display the acquired reference plane image on the corresponding position of the pictogram.

18. The ultrasonic image apparatus of claim 1, wherein the at least one processor is further configured to estimate a position of the ultrasonic probe based on the obtained ultrasound image data.

19. A method of controlling an ultrasonic imaging apparatus, the method comprising steps of:

obtaining ultrasound image data acquired by an ultrasonic probe;

pre-storing a landmark list that should be included in a reference plane, wherein the landmark list includes at least one anatomical feature;

recognizing, from the ultrasound image data, anatomical features that should be included in the landmark list based on a similarity between an object in the ultrasound image data and landmarks in the pre-stored landmark list;

automatically acquiring the ultrasound image data as a reference plane image based on at least a predetermined number of the anatomical features being recognized from the ultrasound image data; and displaying the acquired reference plane image.

20. A non-transitory computer readable recording medium having recorded thereon a program, which, when executed on a computer, causes the computer to perform the steps of the method of claim 19.

* * * * *